(12) United States Patent
Bajramovic et al.

(10) Patent No.: US 9,622,659 B2
(45) Date of Patent: Apr. 18, 2017

(54) METHOD FOR DETERMINING THE TOTAL REFRACTIVE POWER OF THE CORNEA OF AN EYE

(71) Applicant: CARL ZEISS MEDITEC AG, Jena (DE)

(72) Inventors: Ferid Bajramovic, Jena (DE); Janine Feuker, Naumburg/Saale (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 14/440,801

(22) PCT Filed: Nov. 7, 2013

(86) PCT No.: PCT/EP2013/073263
§ 371 (c)(1),
(2) Date: May 5, 2015

(87) PCT Pub. No.: WO2014/072402
PCT Pub. Date: May 15, 2014

(65) Prior Publication Data
US 2015/0265148 A1    Sep. 24, 2015

(30) Foreign Application Priority Data

Nov. 8, 2012 (DE) .......... 10 2012 022 059
Feb. 15, 2013 (DE) .......... 10 2013 002 828

(51) Int. Cl.
*A61B 3/103* (2006.01)
*A61B 3/10* (2006.01)
*A61B 3/107* (2006.01)

(52) U.S. Cl.
CPC .............. *A61B 3/103* (2013.01); *A61B 3/102* (2013.01); *A61B 3/1005* (2013.01); *A61B 3/107* (2013.01); *A61B 3/1035* (2013.01)

(58) Field of Classification Search
CPC .......... A61B 3/107; A61B 3/10; A61B 3/1005; A61B 3/102; A61B 3/1025; A61B 3/1035; A61B 3/103
(Continued)

(56) References Cited

U.S. PATENT DOCUMENTS 6,004,314 A  * 12/1999 Wei .................... A61B 3/102
                                                606/12
2005/0018137 A1    1/2005 Barth et al.
(Continued)

FOREIGN PATENT DOCUMENTS

DE  10 2005 025 221 A1   2/2006
EP       0 928 596 A1    7/1999

OTHER PUBLICATIONS

T. Kawamorita, H. Uozato, K. Kamiya, L. Sax, K. Tsutsui, D. Aizawa, and K. Shimizu, "Repeatability, reproducibility, and agreement characteristics of rotating Scheimpflug photography and scanning-slit corneal topography for corneal power measurement," Journal of Cataract & Refractive Surgery, vol. 35, No. 1, pp. 127-133, Jan. 2009.

(Continued)

*Primary Examiner* — Jordan Schwartz
(74) *Attorney, Agent, or Firm* — Patterson Thuente Pedersen, P.A.

(57) ABSTRACT

A method for determining the total refractive power of the cornea is based on a combination of keratometric or topographic measurements using the measured values obtained from depth scans or sectional images. The radius (Ra) of the front side of the cornea is ascertained keratometrically or topographically, the radius (Rp) of the rear side of the cornea is determined from depth scans or sectional images, and the refractive power (Ka) of the front side of the cornea, the refractive power (Kp) of the rear side of the cornea, and the total refractive power (K) of the cornea are determined. The (Continued)

method is used to determine the total refractive power of the cornea of an eye and is not just applicable to eyes with normal vision but in particular also to astigmatic eyes.

27 Claims, 7 Drawing Sheets

(58) Field of Classification Search
USPC .................................................. 351/212, 246
See application file for complete search history.

(56) References Cited

U.S. PATENT DOCUMENTS

| 2005/0203422 | A1 | 9/2005 | Wei | |
|---|---|---|---|---|
| 2009/0168017 | A1 | 7/2009 | O'Hara et al. | |
| 2011/0222020 | A1* | 9/2011 | Izatt | A61B 3/102 351/205 |
| 2011/0242482 | A1* | 10/2011 | Olsen | A61B 3/0025 351/205 |
| 2012/0016351 | A1* | 1/2012 | Stobrawa | A61F 9/008 606/5 |
| 2012/0140174 | A1 | 6/2012 | Hee et al. | |
| 2013/0107208 | A1* | 5/2013 | Endo | A61B 3/10 351/206 |
| 2013/0188140 | A1* | 7/2013 | Bagherinia | A61B 3/102 351/206 |

OTHER PUBLICATIONS

Tang M. et al., "Measuring Total Corneal Power Before and After Laser in Situ Keratomileusis with High-Speed Optical Coherence Tomography" Journal Cataract and Refractive Surgery, vol. 32, No. 11, pp. 1843-1850 Nov. 1, 2006.

Tang M. et al., "Corneal power measurement with Fourier domain optical coherence tomography," J Cataract Refract Surg, vol. 36, No. 12, pp. 2115-2122, Dec. 2010.

L. Wang, A.M. Mahmoud, . L. Anderson, D.D. Koch, and C.J. Roberts, "Total corneal power estimation: ray tracing method versus Gaussian optics formula," Invest. Ophthalmol. Vis. Sci., vol. 52, No. 3, pp. 1716-1722, Mar. 2011.

M. Tang, L. Wang, D. D. Koch, Y. Li, and D. Huang, "Intraocular lens power calculation after myopic and hyperopic laser vision correction using optical coherence tomography," Saudi Journal of Ophthalmology, vol. 26, No. 1, pp. 19-24, Jan. 2012.

T. Olsen, "On the calculation of power from curvature of the cornea", British Journal of Ophthalmololgy, vol. 70, No. 2, pp. 152-154, Feb. 1986.

L.N. Thibos and D. Horner, "Power vector analysis of the optical outcome of refractive surgery," Journal of Cataract & Refractive Surgery, vol. 27, No. 1, pp. 80-85, Jan. 2001.

R. Navarra, L. Gonzalez, and J.L. Hernandez, "Optics of the average normal cornea from general and canonical representations of its surface topography," J Opt Soc Am A Opt Image Sci Vis, vol. 23, No. 2, pp. 219-232, Feb. 2006.

PCT International Search Report with English translation for PCT/EP2013/073263, mailed Feb. 5, 2014, 7 pgs.

DE Search Report (9 pages) with English translation (6 pages) for DE 10 2012 022 059.6, mailed Nov. 13, 2014.

DE Search Report (5 pages) with English translation (5 pages) for DE 10 2013 002 828.0, mailed Mar. 27, 2014.

Notification of transmittal of Translation of the International Preliminary Report on Patentability for International Application No. PCT/EP2012/073263, mailed May 21, 2015, 9 pages.

* cited by examiner

Fig. 1 (part A)

```
┌─────────────────────────────────────┐
│ Method for determining the total    │
│ refractive power of the cornea of   │
│ an eye from the measured values of  │
│ a keratometric or topographical     │
│ measurement as well as the          │
│ measured values obtained from       │
│ depth scans or sectional images     │
└─────────────────────────────────────┘
``` the radius $R_a$ of the anterior cornea side is measured keratometrically or topographically, and from this measurement, the refractive power $Ka$ of the anterior cornea side is determined as follows:

$$Ka = \frac{n1 - n0}{Ra} \quad (1)$$

b) the radius $R_p$ of the posterior cornea side is determined from depth scans or sectional images, and from this determination, the refractive power $K_p$ of the posterior cornea side is determined as follows:

$$Kp = \frac{n2 - n1}{Rp} \quad (2)$$

c) the central thickness d of the cornea is determined from depth scans or sectional images, and afterward, the total refractive power K of the cornea is determined as follows:

$$K = Ka + Kp - \frac{d}{n1} Ka Kp \quad (3)$$

the radius $R'_p$ of the posterior cornea side, determined from depth scans or sectional images, does not enter directly into the calculation of the total refractive power K according to method step c) as a measured value, but rather is taken into consideration in an additional step:

d) determined anterior/posterior ratio c taken into consideration:

$$R_p = c * R_a \quad (4)$$

with $\quad c = \frac{R'p}{R'a}$ in that the radii $R'_a$ and $R'_p$ are determined from depth scans or sectional images, and $R_p$ represents a resulting measured value from a keratometric or topographical measurement and from a depth scan measurement or sectional image measurement.

A

Fig. 1 (part B)

Fig.1 (part C)

Fig. 2 (part A)

B⟶ wherein radii $R'_{p1}$ and $R'_{p2}$ of the posterior cornea side determined from depth scans or sectional images do not enter directly into the calculation of the total refractive power $K_1$ and $K_2$ according to method step c), as a measured value, but rather are taken into consideration in an additional step:

d) determined anterior/posterior ratios $c_1$ and $c_2$ taken into consideration:

$$R_{p1} = c_1 * R_{a1}$$
$$R_{p2} = c_2 * R_{a2}$$

(4)

with $$c1 = \frac{R'_{p1}}{R'_{a1}}$$

$$c2 = \frac{R'_{p2}}{R'_{a2}}$$

in that the radii $R'_a$ and $R'_p$ are determined from depth scans or sectional images, and $R_p$ represents a resulting measured value from a keratometric or topographical measurement and from a depth scan or sectional image measurement.

Fig. 2 (part B)

Fig. 2 (part C)

B → wherein the measured values are arithmetically averaged after prior removal of "outliers" and then entered into the calculation of the total refractive powers $K_1$ and $K_2$ according to method step c).

B → wherein the depth scan measurement or sectional image measurement of the radii of the cornea takes place by means of image processing, in that functions are fitted to the anterior and posterior side of the cornea, for example.

B → wherein a circle is fitted to the anterior and posterior side of the cornea, in each instance, which circle preferably lies symmetrical to the vertex B → wherein a sphere is fitted to the anterior and posterior side of the cornea, on depth scans or sectional images taken along multiple meridians, which sphere preferably lies symmetrical to the vertex.

B → wherein depth scan measurements take place on an OCT basis, in that at least one B scan is implemented along one meridian, but preferably multiple B scans are performed along multiple meridians B ⟶ wherein sectional image measurements take place using Scheimpflug cameras or also slit lamps, in that images are recorded along at least one meridian and preferably along multiple meridians.

Fig. 2 (part D)

METHOD FOR DETERMINING THE TOTAL REFRACTIVE POWER OF THE CORNEA OF AN EYE

RELATED APPLICATIONS

This application is a National Phase entry of PCT Application No. PCT/EP2013/073263 filed Nov. 7, 2013, which application claims the benefit of priority to German Application No. 10 2013 002 828.0, filed Feb. 15, 2013 and claims the benefit of priority to German Application No. 10 2012 022 059.6 filed Nov. 8, 2012, the entire disclosures of which are incorporated herein by reference.

BACKGROUND

The present invention relates to a method for determining the total refractive power of the cornea of an eye, and is based on a combination of keratometric or topographical measurements with the measured values obtained from depth scans or sectional images. The total refractive power of the cornea is particularly significant also with regard to the calculation and selection of intraocular lenses.

According to the known state of the art, numerous solutions are known for this purpose.

For highly precise measurement in the form of depth scans, solutions have established themselves in the state of the art, which are based on the method of optical coherence tomography (OCT), partial coherence interferometry (PCI) or the like.

The fundamental principle of the OCT method is based on white light interferometry and compares the running time of a signal using an interferometer (generally a Michelson interferometer). In this connection, the arm having the known optical path length (=reference arm) is used as a reference for the measurement arm. The interference of the signals from both arms yields a pattern from which the relative optical path length within an A scan (individual depth signal) can be read out. In the one-dimensional raster methods, the beam is then guided transversally in one or also in two directions, analogous to the ultrasound technique, thereby making it possible to record a two-dimensional B scan or a three-dimensional tomogram (C scan). In this connection, the amplitude values of the individual A scans are typically represented as logarithmic gray-scale or false-color values.

In contrast to this, sectional images can be produced using Scheimpflug cameras or also slit lamps.

A Scheimpflug camera is based on adherence to what is called the Scheimpflug rule, according to which rule the image plane, lens plane, and focal plane must intersect in a common straight line, so that the entire object plane is imaged with maximal focus. With regard to the implementation of sectional images for determining the total refractive power of the cornea of an eye, the advantage of the camera is rooted in the fact that the entire object plane of the section through the cornea is imaged with sharp focus, and the recorded images do not contain any blurring.

A slit lamp (also: slit lamp microscope) is one of the most important ophthalmological examination instruments, with which an eye doctor or optician can inspect the eyes stereoscopically. The examining person has the possibility of directing a sharply delimited slit-shaped beam of light, the width of which can be changed, onto the eye. At the same time, he/she has the possibility of observing the eye through the incident light microscope. The enlargement of the microscope is variable, in most of the devices, and usually ranges from 6 times to 30 times.

By means of different lighting methods (diffuse, direct, focal, indirect, regressive, lateral, etc.) and variable light slit widths, it is possible to inspect almost all the anterior, central, and posterior sections of the eye, all the way to areas of the retina situated far in the periphery. For many examinations, additional aids, such as, for example, a three-mirror contact lens, are required. Most modern slit lamps have a digital camera for documenting findings on film or in photographs.

If, however, additional measurement variables are needed, these can be determined, for example, from keratometric or topographical recorded images of the eye.

It is true that these further measurement variables and the OCT measured values can be measured by application of different devices, but integration of the measurement both of OCT and of the further measurement variables in one device allows easier handling, for example only one-time alignment of the device relative to the patient, and improved lateral registration of the OCT measured values with the further measured values.

In a first group of solutions, the different images are recorded sequentially, i.e., one after the other.

An example is shown by US 2005/0203422 A1, which shows a combination system of a keratometer and OCT tomography. In order to separate the two modalities from one another, separation in terms of time is also proposed here.

A further example is the IOLMaster from the Carl Zeiss company. This is a combination device that determines the keratometry, the axial length by way of PCI (partial coherence interferometry), and the anterior chamber depth by way of slit illumination and image detection, as well as further parameters of the eye, such as what is called the white-to-white distance.

In all of these measurements that take place sequentially, the time expended for the measurements is greater. It is furthermore disadvantageous that the different measurements of OCT and ultrasound or keratometry could take place at slightly different locations because of possible eye movements. In general, reproducibility of the measurement is accordingly difficult to implement.

In a second group of solutions, the different images are recorded at the same time, and for this, the measurement systems must have corresponding optical separation at their disposal.

As a further example, a combination system composed of a keratometer and axial length measurement by means of PCI is described in US 2005/0018137 A1. In this connection, the separation of the two modalities is implemented by beam splitting by means of polarization separation.

The document US 2005/0203422 A1, which has already been mentioned above, also mentions separation of the modalities (by means of OCT and keratometry), by means of a dichroic beam splitter, as an alternative to sequential measurement.

In all of these examples, optical separation of the different measurement systems takes place either by means of the use of different wavelengths or by way of additional optical elements that prevent the measurement systems from reciprocally influencing one another.

It is a disadvantage in the techniques described above that the traditional methods of keratometry and topography measure only the radius $R_a$ of the anterior cornea side, and determine the total refractive power $K_{Ker}$ of the cornea, including the optical effect of the posterior side, from this measurement by approximation. According to the literature [7], the total refractive power $K_{Ker}$ is calculated as follows:

$$KKer = \frac{nK - 1}{Ra} \quad (0)$$

The assumptions concerning cornea thickness and anterior/posterior side ratio, as well as their indices of refraction, are implicitly included in the value $n_k$.

Other approaches measure the total refractive power of the cornea without assumptions concerning the anterior/posterior side ratio and/or cornea thickness, by means of using OCT or a combination of OCT and topography. Good reproducibility of the measurement of the cornea radii by means of OCT is difficult to achieve. In particular, high scanning speeds and resolutions are required due to possible eye movements during the measurement. For a correct measurement of the radii, precise calibration of the OCT (including scanner) is required. This also holds true in combination with topography.

For selection of an intraocular lens (IOL) by means of the IOL calculation formula, the empirical knowledge of the ULIB database is frequently accessed, in practice. For this purpose, it is necessary that the measured total refractive power of the cornea, on the average of the population having normal eyes, agrees with the measured values of the keratometer of the IOLMaster.

This is not the case for existing approaches for determining the total refractive power of the cornea of an eye, or at least has not been proven.

LITERATURE

[1] M. Tang, Y. Li, M. Avila, and D. Huang, "Measuring total corneal power before and after laser in situ keratomileusis with high-speed optical coherence tomography," J Cataract Refract Surg, vol. 32, no. 11, pp. 1843-1850, November 2006.

[2] M. Tang, A. Chen, Y. Li, and D. Huang, "Corneal power measurement with Fourier domain optical coherence tomography," J Cataract Refract Surg, vol. 36, no. 12, pp. 2115-2122, December 2010.

[3] L. Wang, A. M. Mahmoud, 8. L. Anderson, D. D. Koch, and C. J. Roberts, "Total corneal power estimation: ray tracing method versus Gaussian optics formula," Invest. Ophthalmol. Vis. Sci., vol. 52, no. 3, pp. 1716-1722, March 2011.

[4] T. Kawarnorita, H. Uozato, K. Kamiya, L. Sax, K. Tsutsui, D. Aizawa, and K. Shimizu, "Repeatability, reproducibility, and agreement characteristics of rotating Scheimpflug photography and scanning-slit corneal topography for corneal power measurement," Journal of Cataract & Refractive Surgery, vol. 35, no. 1, pp. 127-133, January 2009.

[5] M. Tang, L. Wang, D. D. Koch, Y. Li, and D. Huang, "Intraocular lens power calculation after myopic and hyperopic laser vision correction using optical coherence tomography," Saudi Journal of Ophthalmology, vol. 26, no. 1, pp. 19-24, January 2012.

[6] M. Tang, Y. Li, M. Avila, and D. Huang, "Measuring total corneal power before and after laser in situ keratomileusis with high-speed optical coherence tomography," Journal of Cataract & Refractive Surgery, vol. 32, no. 11, pp. 1843-1850, 2006.

[7] T. Olsen, "On the calculation of power from curvature of the cornea," Br J Opthalmol, vol. 70, no. 2, pp. 152-154, February 1986.

[8] L. N. Thibos and D. Horner, "Power vector analysis of the optical outcome of refractive surgery," Journal of Cataract & Refractive Surgery, vol. 27, no. 1, pp. 80-85, January 2001.

[9] R. Navarra, L. Gonzalez, and J. L. Hernandez, "Optics of the average normal cornea from general and canonical representations of its surface topography," J Opt Soc Am A Opt Image Sci Vis, vol. 23, no. 2, pp. 219-232, February 2006.

SUMMARY OF THE INVENTION

The present invention is based on the task of developing a method for determining the total refractive power of the cornea of an eye, which method abstains from the assumption of normal values and, in particular, can also be used for determining the total refractive power of the laser-treated cornea of an eye.

This task is accomplished by application of the method according to the invention for determining the total refractive power of the cornea of an eye, based on the measured values of a keratometric or topographical measurement as well as the measured values obtained from depth scans or sectional images, in accordance with the following method steps, in that:

a) the radius $R_a$ of the anterior cornea side is measured keratometrically or topographically, and from this measurement, the refractive power $K_a$ of the anterior cornea side is determined as follows:

$$Ka = \frac{n1 - n0}{Ra} \quad (1)$$

b) the radius $R_p$ of the posterior cornea side is determined from depth scans or sectional images, and from this determination, the refractive power $K_p$ of the posterior cornea side is determined as follows:

$$Kp = \frac{n2 - n1}{Rp} \quad (2)$$

c) the central thickness d of the cornea is determined from depth scans or sectional images, and afterward, the total refractive power K of the cornea is determined as follows:

$$K = Ka + Kp - \frac{d}{n1} KaKp \quad (3)$$

in which

K defines the total refractive power of the cornea, $K_a$ defines the refractive power of the anterior cornea side, $K_p$ defines the refractive power of the posterior cornea side, $R_a$ defines the radius of the anterior cornea side, $R_p$ defines the radius of the posterior cornea side, $n_0$ defines the index of refraction of air, $n_1$ defines the index of refraction of the cornea,
$n_2$ defines the index of refraction of the aqueous fluid, and
d defines the central thickness of the cornea,
wherein the radii $R_a$, $R_p$ and the thickness d are indicated in meters, and the refractive powers K, $K_a$, and $K_p$ are indicated in diopters.

The method according to an embodiment of the invention serves for determining the total refractive power of the cornea of an eye and is based on a combination of keratometric or topographical measurements with the measured values obtained from depth scans or sectional images. In this connection, the method can be used not only for eyes having normal vision but also for astigmatic eyes.

DETAILED DESCRIPTION

The invention will be described in greater detail below, using exemplary embodiments.

Figure 1:
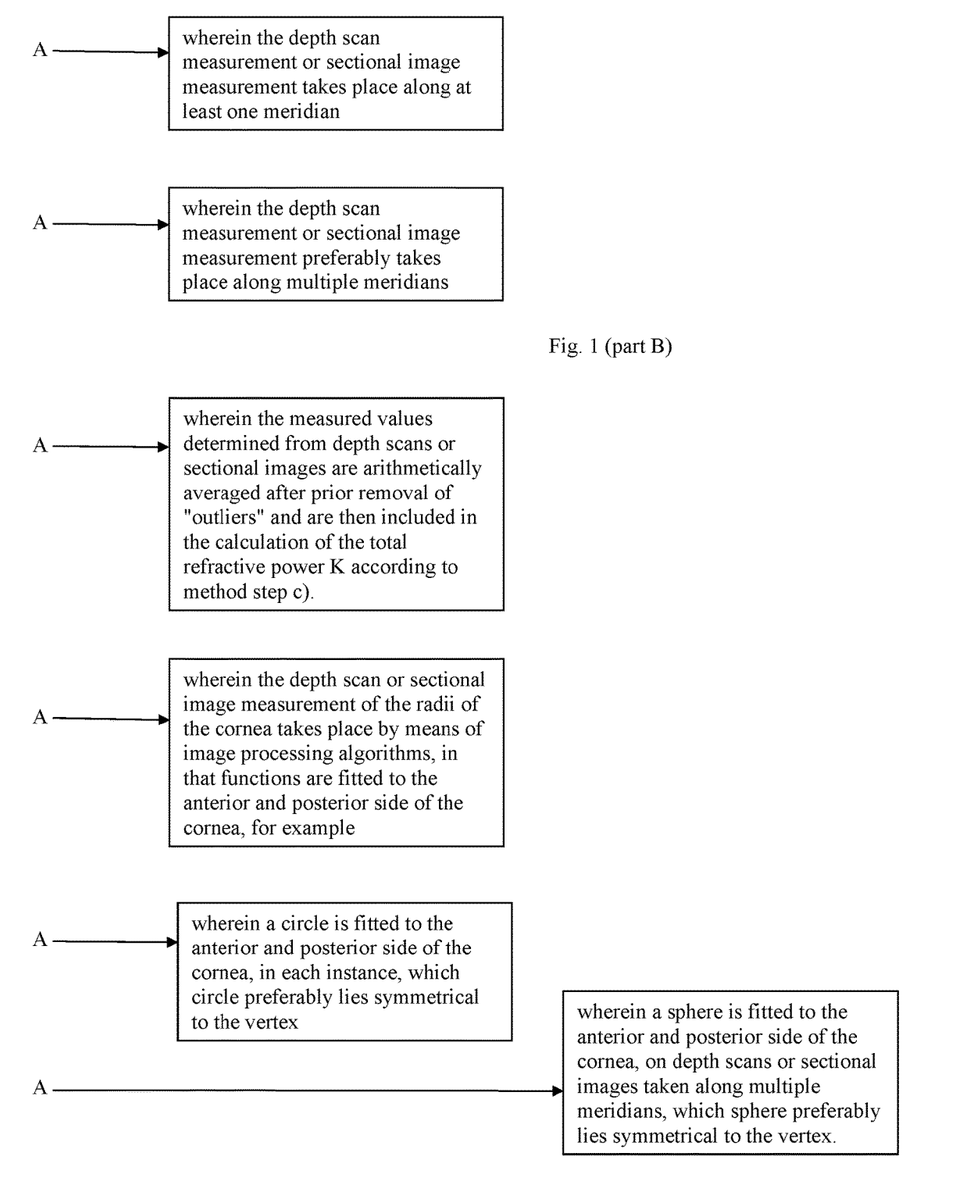
FIG. 1 is a flow chart depicting a method according to an example embodiment of the invention.

The method according to the invention for determining the total refractive power of the cornea of an eye is based on the measured values of a keratometric or topographical measurement as well as the measured values obtained from depth scans or sectional images. In detail, in this connection, in accordance with the following method steps:

a) the radius $R_a$ of the anterior cornea side is measured keratometrically or topographically, and from this measurement, the refractive power $K_a$ of the anterior cornea side is determined as follows:

$$Ka = \frac{n1 - n0}{Ra} \quad (1)$$

b) the radius $R_p$ of the posterior cornea side is determined from depth scans or sectional images, and from this determination, the refractive power $K_p$ of the posterior cornea side is determined as follows:

$$Kp = \frac{n2 - n1}{Rp} \quad (2)$$

c) the central thickness d of the cornea is determined from depth scans or sectional images, and afterward, the total refractive power K of the cornea is determined as follows:

$$K = Ka + Kp - \frac{d}{n1} KaKp \quad (3)$$

in which
K defines the total refractive power of the cornea,
$K_a$ defines the refractive power of the anterior cornea side,
$K_p$ defines the refractive power of the posterior cornea side,
$R_a$ defines the radius of the anterior cornea side,
$R_p$ defines the radius of the posterior cornea side,
$n_0$ defines the index of refraction of air,
$n_1$ defines the index of refraction of the cornea,
$n_2$ defines the index of refraction of the aqueous fluid, and
d defines the central thickness of the cornea,
wherein the radii $R_a$, $R_p$ and the thickness d are indicated in meters, and the refractive powers K, $K_a$, and $K_p$ are indicated in diopters.

According to the statements made by T. Olsen in [7], with regard to determining the refractive power of the cornea, the description of the total refractive power K of the cornea also takes place, in this connection, by use of a paraxial lens (also called a "thick lens") approach.

In this connection, the following typical values serve as a prerequisite for the indices of refraction:
index of refraction of air $n_0=1$,
index of refraction of the cornea $n_1=1,376$, and
index of refraction of the aqueous fluid $n_2=1.336$.

In contrast to the solutions of the state of the art, which are based on various traditional measurement methods with corresponding assumptions, in the method proposed here not only the radius of the anterior cornea side $R_a$ but also the radius of the posterior cornea side $R_p$ are measured.

While the radius of the anterior cornea side $R_a$ is measured keratometrically or topographically, the determination of the other measured values, such as the radius of the posterior cornea side $R'_p$ and the central thickness d of the cornea, takes place by means of depth scans or sectional images.

According to an example embodiment of the invention, the radius $R'_p$ of the posterior cornea side, determined from depth scans or sectional images, does not enter directly into the calculation of the total refractive power K according to method step c) as a measured value, but rather is taken into consideration in an additional step:

d) determined anterior/posterior ratio c taken into consideration:

$$R_p = c*R_a \quad (4)$$

with $$C = \frac{R\prime p}{R\prime a}$$

in that the radii $R'_a$ and $R'_p$ are determined from depth scans or sectional images, and $R_p$ represents a resulting measured value from a keratometric or topographical measurement and from a depth scan or sectional image measurement. In the calculation of the total refractive power K, the anterior/posterior side ratio c is taken into consideration, according to the formula (4).

This method of procedure has the advantage that the demands on correct behavior of the scanners and on precise optics adjustment can be clearly reduced. Furthermore, it is possible to do without measurement of the actual scanner behavior.

Errors in the measured values of the radii determined from depth scans or sectional images can be expressed as follows:

$$R'_a = x_a \cdot R_a \text{ and}$$

$$R'_p = x_p \cdot R_p \text{ with}$$

$$x_a, x_p \neq 0 \quad (5)$$

If the factors $x_a$ and $x_p$ are the same ($x_a=x_p$), then the anterior/posterior side ratio c determined from the depth scans or sectional images is correct in every case, because the factors cancel one another out in formula (4). Such errors therefore have no influence on determining the total refractive power K.

Other types of errors for which $x_a \ne x_p$ holds true do have an effect both on the anterior/posterior side ratio c and on the total refractive power K of the cornea, but the resulting error is slight, because only the ratio $x_p/x_a \approx 1$ enters into c and K. This particularly holds true for linear errors in the radii determined from depth scans or sectional images, which can be described as follows:

$$R'_a = x_a \cdot R_a + y \text{ and}$$

$$R'_p = x_p \cdot R_p + y \text{ with}$$

$$|y| << |x_a \cdot R_a| \quad (6)$$

In a further example embodiment of the method according to the invention, the depth scan or sectional image measurement takes place along at least one meridian.

Although this method of procedure should be sufficient for eyes having normal vision, the precision of the determination of the total refractive power of the cornea of an eye can be additionally increased if the depth scan or sectional image measurement takes place preferably along multiple meridians.

If therefore more than one measured value is present for $R'_a$, $R'_p$ and/or d, then the measured values determined from depth scans or sectional images are arithmetically averaged after prior removal of "outliers" and are then included in the calculation of the total refractive power K according to method step c).

According to the invention, the depth scan or sectional image measurements of the radii of the cornea take place in that image processing algorithms are used. For example, functions can be fitted to the anterior and posterior side of the cornea. Preferably, in this connection, a circle is fitted to the anterior and posterior side of the cornea, in each instance, which circle particularly preferably lies symmetrical to the vertex. According to another example, in this connection, if a sphere is fitted to the anterior and posterior side of the cornea, on the depth scans or sectional images taken along multiple meridians, which sphere preferably also lies symmetrical to the vertex.

Preferably, in this connection, fitting takes place to a zone that is either 6 mm wide or corresponds to the zone in which the radius $R_a$ of the anterior cornea side is measured.

In this connection, it should be noted that fitting of polynomials and determination of the radius of curvature at the vertex generally leads to systematically deviating measurements of the radii and also of the anterior/posterior side ratio.

In another example embodiment, the method according to the invention is used for determining the total refractive power of the cornea of an astigmatic eye. For this purpose, measured values from a keratometric or topographical measurement as well as from depth scan or sectional image measurements that are obtained along two meridians are also used, wherein these correspond to the main sections determined previously.

For the selection of a toric IOL for compensation of an astigmatic eye defect, measurement of the cornea refractive powers $K_1$ and $K_2$ along the two main sections and the related axis position a are required. According to the solutions of the state of the art, established methods measure the two radii $R_{a1}$ and $R_{a2}$ and the angle $\alpha_a$ of the anterior cornea side for this purpose, and calculate the total refractive powers $K_1$ and $K_2$ under certain assumptions.

According to an example embodiment of the invention, however, it is desirable here, as well, to take the values of the posterior cornea side and the thickness into consideration by means of explicit measurement. In this connection, one proceeds from the assumption that the main sections determined on the anterior side of the cornea also apply to the posterior side or for the cornea as a whole.

Figure 2:
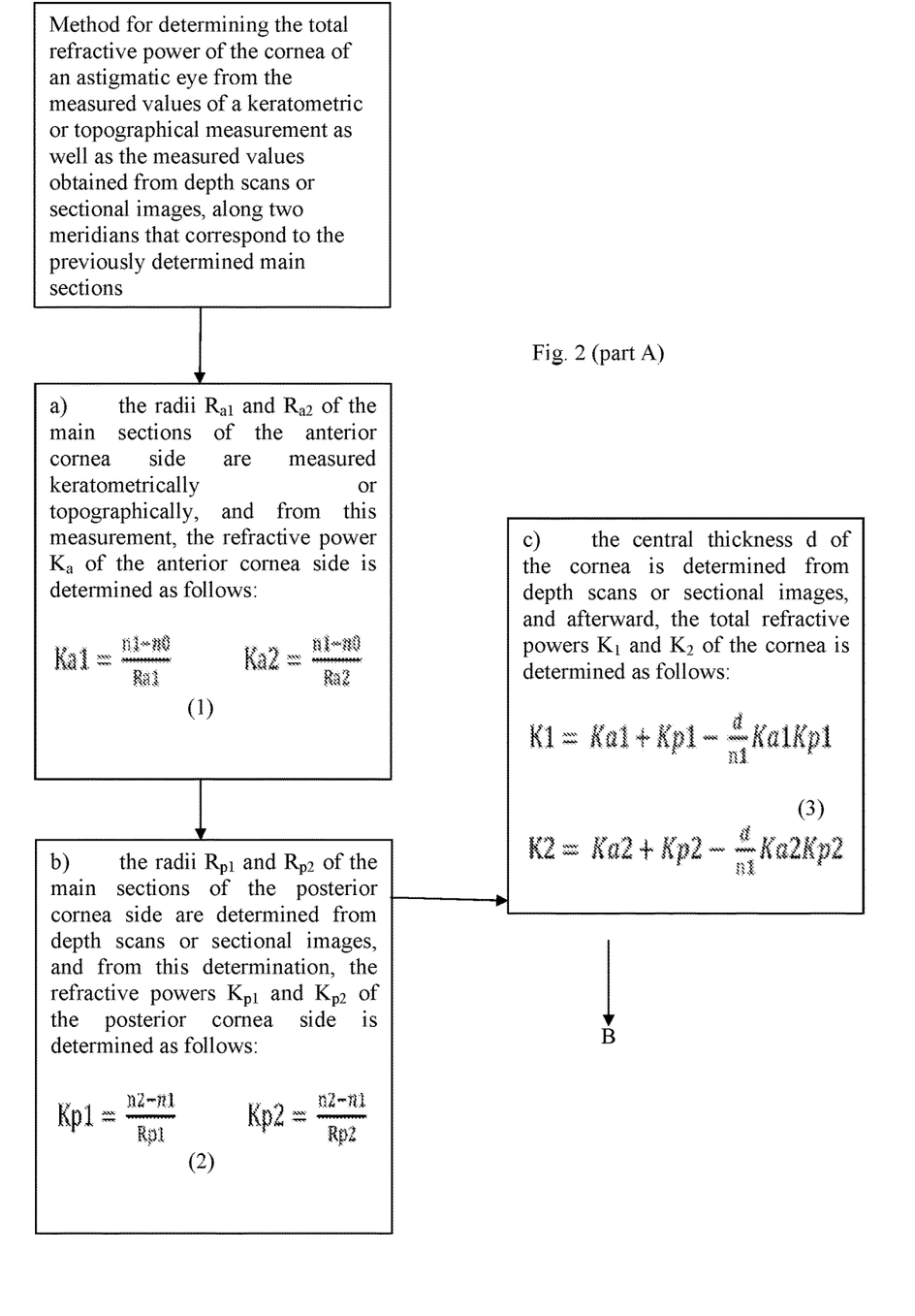
FIG. 2 is a flow chart depicting a method according to another example embodiment of the invention.

To determine the total refractive power of the cornea of an astigmatic eye, the following method steps are followed, in detail:

a) the radii $R_{a1}$ and $R_{a2}$ of the main sections of the anterior cornea side are measured keratometrically or topographically, and from this measurement, the refractive power $K_a$ of the anterior cornea side is determined as follows:

$$Ka1 = \frac{n1 - n0}{Ra1} \quad (1)$$

$$Ka2 = \frac{n1 - n0}{Ra2}$$

b) the radii $R_{p1}$ and $R_{p2}$ of the main sections of the posterior cornea side are determined from depth scans or sectional images, and from this determination, the refractive powers $K_{p1}$ and $K_{p2}$ of the posterior cornea side are determined as follows:

$$Kp1 = \frac{n2 - n1}{Rp1} \quad (2)$$

$$Kp2 = \frac{n2 - n1}{Rp2}$$

c) the central thickness d of the cornea is determined from depth scans or sectional images, and afterward, the total refractive powers $K_1$ and $K_2$ of the cornea are determined as follows:

$$K1 = Ka1 + Kp1 - \frac{d}{n1} Ka1 Kp1 \quad (3)$$

$$K2 = Ka2 + Kp2 - \frac{d}{n1} Ka2 Kp2$$

in which
$K_{1,2}$ define the total refractive power of the cornea,
$K_{a1,2}$ define the refractive power of the anterior cornea side,
$K_{p1,2}$ define the refractive power of the posterior cornea side,
$R_{a1,2}$ define the radius of the anterior cornea side,
$R_{p1,2}$ define the radius of the posterior cornea side,
$n_0$ defines the index of refraction of air,
$n_1$ defines the index of refraction of the cornea,
$n_2$ defines the index of refraction of the aqueous fluid, and
d defines the central thickness of the cornea,
wherein the radii $R_a$, $R_{p1,2}$ and the thickness d are indicated in meters, and the refractive powers $K_{1,2}$, $K_{a1,2}$, and $K_{p1,2}$ are indicated in diopters.

Here, too, the aforementioned typical values serve as a prerequisite for the indices of refraction:

index of refraction of air $n_0=1$,
index of refraction of the cornea $n_1=1.376$, and
index of refraction of the aqueous fluid $n_2=1.336$.

In contrast to the solutions of the state of the art, which are based on various traditional measurement methods with corresponding assumptions, in the method proposed here not only the radii of the anterior cornea side $R_{a1}$ and $R_{a2}$ but also the radii of the posterior cornea side $R_{p1}$ and $R_{p2}$ are measured.

While the radii of the anterior cornea side $R_{a1}$ and $R_{a2}$ are measured keratometrically or topographically, the determination of the other measured values, such as the radii of the posterior cornea side $R'_{p1}$ and $R'_{p2}$, as well as the central thickness d of the cornea, takes place by means of depth scans or sectional images.

According to an embodiment of the invention, here, too, the radii $R'_{p1}$ and $R'_{p2}$ of the posterior cornea side, determined from depth scans or sectional images, do not enter directly into the calculation of the total refractive power $K_1$ and $K_2$ according to method step c), as measured values, but rather are taken into consideration in an additional step:

d) determined anterior/posterior ratios $c_1$ and $c_2$ taken into consideration:

with $$R_{p1} = c_1 * R_{a1} \quad (4)$$

$$R_{p2} = c_2 * R_{a2}$$

with $$c1 = \frac{R'p1}{R'a1}$$

$$c2 = \frac{R'p2}{R'a2}$$

in that the radii $R'_a$ and $R'_p$ are determined from depth scans or sectional images, and $R_p$ represents a resulting measured value from a keratometric or topographical measurement and from a depth scan or sectional image measurement. In the calculation of the total refractive power K, the anterior/posterior side ratio c is taken into consideration, according to the formula (4).

For the calculation of the total refractive powers $K_1$ and $K_2$, the radii $R_{p1}$ and $R_{p2}$ of the posterior cornea side are determined from the anterior/posterior side ratios $c_i$ and $c_2$, by rearrangement of the formulas (4).

With regard to the requirements concerning correct behavior of the scanners and regarding precise optics adjustment, as well as errors that occur in the measured values determined from depth scans or sectional images, what was described above applies analogously.

Because here, more than one measured value is necessarily present for $R_{a1}$, $R_{a2}$, $R_{p1}$, $R_{p2}$ and/or d, the measured values obtained from depth scans or sectional images are arithmetically averaged here, too, after prior removal of "outliers," and then enter into the calculation of the total refractive powers $K_{1,2}$.

According to the invention, here, too, the depth scan or sectional image measurement of the radii of the cornea takes place in that image processing algorithms are used. For example, functions can be fitted to the anterior and posterior side of the cornea. Preferably, in this connection, a circle is fitted, in each instance, which preferably lies symmetrical to the vertex. According to another example embodiment a sphere is fitted to the anterior and posterior side of the cornea, on the depth scans or sectional images taken along multiple meridians, which sphere preferably also lies symmetrical to the vertex.

According to a further embodiment of the method according to the invention, it is possible to implement measurements not only along the main sections determined previously, but rather along multiple meridians, and to construct a height map of the posterior cornea side from this. This is possible either purely from depth scan measurements or sectional image measurements or by means of a combination of keratometry/topography and pachymetry (from OCT). A detailed description can be derived from the literature reference [6].

According to the invention, in the proposed method depth scan measurements take place on an OCT basis, in that at least one B scan is implemented along one meridian, but preferably multiple B scans are performed along multiple meridians.

Sectional image measurements take place in the method according to the invention, using Scheimpflug cameras or also slit lamps, in that images are recorded along at least one meridian and preferably along multiple meridians.

Measurement of the asphericity, i.e., what is called the "shape factor," is possible and furthermore usual both for topography machines and for keratometers having more than one measurement zone. If conclusions concerning the optical properties of the cornea, such as the spherical aberrations, for example, are to be drawn from this shape parameter, a measurement of the contribution of the posterior cornea side is desirable. Accordingly, the method described above for toric measurement can also be used accordingly for asphericity. In place of a toric view, an aspheric view must then be used for both surfaces. The combination of the optical effects of the two cornea surfaces is accordingly generalized by means of ray tracing, for example.

With the solution according to the invention, a method is made available, with which the total refractive power of the cornea of an eye can be determined precisely.

The method does without the assumption of normal values and can furthermore be used for determining the total refractive power of the laser-treated cornea of an eye.

According to an example embodiment of the invention, the radius $R_p$ of the posterior cornea side, determined from depth scans or sectional images, does not enter directly into the calculation of the total refractive power K as a measured value, but rather from the previously determined anterior/posterior side ratio c.

This method has the advantage that the requirements concerning correct behavior of the scanners and concerning precise optics adjustment can be clearly reduced. Furthermore, it is possible to do without measurement of the actual scanner behavior.

Furthermore, errors in the measured values determined from depth scans or sectional images only have a slight influence or no influence at all on the determination of the total refractive power K. Therefore the requirements concerning the precision of certain aspects of data collection and evaluation are clearly lower than in the case of the solutions known from the state of the art.

The invention claimed is:

1. A method for determining total refractive power of a cornea of an eye from measured values of a keratometric or topographical measurement as well as measured values obtained from depth scans or sectional images, comprising:
    a) measuring a radius $R_a$ of an anterior cornea side keratometrically with a first modality comprising a keratometer or topographically with a topographer to acquire a measurement, and from the measurement, determining a refractive power Ka of the anterior cornea side as follows:

$$Ka = \frac{n1 - n0}{Ra} \quad (1)$$

b) determining a radius $R_p$ of a posterior cornea side at least partially with a second modality performing depth scans or sectional images, and from this determination, a refractive power $K_p$ of the posterior cornea side as follows:

$$Kp = \frac{n2 - n1}{Rp} \quad (2)$$

c) determining a central thickness d of the cornea from depth scans or sectional images, and afterward, determining a total refractive power K of the cornea as follows:

$$K = Ka + Kp - \frac{d}{n1} KaKp \quad (3)$$

in which K defines the total refractive power of the cornea,
  $K_a$ defines the refractive power of the anterior cornea side,
  $K_p$ defines the refractive power of the posterior cornea side,
  $R_a$ defines the radius of the anterior cornea side,
  $R_p$ defines the radius of the posterior cornea side,
  $n_0$ defines an index of refraction of air,
  $n_1$ defines an index of refraction of the cornea,
  $n_2$ defines an index of refraction of aqueous fluid, and
  d defines the central thickness of the cornea,
wherein the radii $R_a$, $R_p$ and the thickness d are indicated in meters, and the refractive powers K, $K_a$, and $K_p$ are indicated in diopters.

2. The method according to claim 1, further wherein $R_p$ is further determined by
  d) taking into consideration a determined anterior/posterior ratio c as follows:

$$R_p = c * R_a \quad (4)$$

with $$c = \frac{R'p}{R'a}$$

wherein $R'_a$ is a radius of the anterior corneal side determined from depth scans or sectional images and $R'_p$ is a radius of the posterior corneal side determined from depth scans or sectional images, and wherein $R_p$ represents a resulting value determined from the keratometric or the topographical measurement of $R_a$ and from a depth scan or sectional image determinations of both $R'_a$ and $R'_p$.

3. The method according to claim 1, further comprising taking the depth scan measurement or sectional image measurement along at least one meridian.

4. The method according to claim 2, further comprising taking the depth scan measurement or sectional image measurement along at least one meridian.

5. The method according to claim 1, further comprising taking the depth scan measurement or sectional image measurement along multiple meridians.

6. The method according to claim 1, further comprising arithmetically averaging the measured values determined from depth scans or sectional images after prior removal of "outliers" and then including arithmetically averaged values in the calculation of the total refractive power K according to method step c).

7. The method according to claim 1, wherein the depth scan or sectional image measurement of the radii of the cornea takes place by application of image processing algorithms.

8. The method according to claim 7, further comprising fitting functions to the anterior and posterior side of the cornea.

9. The method according to claim 1, further comprising fitting a circle to the anterior and posterior side of the cornea.

10. The method according to claim 9, wherein the circle lies symmetrical to a vertex.

11. The method according to claim 1, further comprising fitting a sphere to the anterior and posterior side of the cornea, on depth scans or sectional images taken along multiple meridians.

12. The method according to claim 11, wherein the sphere lies symmetrical to a vertex.

13. The method according to claim 1, further comprising taking depth scan measurements on an OCT basis, and wherein at least one B scan is implemented along one meridian.

14. The method according to claim 13, wherein multiple B scans are performed along multiple meridians.

15. The method according to claim 1, further comprising recording sectional image measurements using Scheimpflug cameras or slit lamps, wherein the sectional images are recorded along at least one meridian.

16. The method according to claim 1, wherein the sectional images are recorded along multiple meridians.

17. A method for determining the total refractive power of a cornea of an astigmatic eye from measured values of a keratometric or a topographical measurement as well as measured values obtained from depth scans or sectional images, along two meridians including a first meridian and a second meridian that correspond to previously determined main sections, comprising:
  a) measuring radii $R_{a1}$ and $R_{a2}$ of the main sections of an anterior cornea side keratometrically with a first modality comprising a keratometer or topographically with a topographer, and from this measurement, determining refractive power $K_a$ of the anterior cornea side as follows:

$$Ka1 = \frac{n1 - n0}{Ra1} \quad (1)$$

$$Ka2 = \frac{n1 - n0}{Ra2}$$

b) determining radii $R_{p1}$ and $R_{p2}$ of the main sections of a posterior cornea side at least partially with a second modality performing depth scans or sectional images, and from this determination, determining the refractive powers $K_{p1}$ and $K_{p2}$ of the posterior cornea side as follows:

$$Kp1 = \frac{n2 - n1}{Rp1} \quad (2)$$

-continued $$Kp2 = \frac{n2-n1}{Rp2}$$

c) determining a central thickness d of the cornea from depth scans or sectional images, and afterward, determining total refractive powers $K_1$ and $K_2$ of the cornea as follows:

$$K1 = Ka1 + Kp1 - \frac{d}{n1}Ka1Kp1 \quad (3)$$

$$K2 = Ka2 + Kp2 - \frac{d}{n1}Ka2Kp2$$

in which $K_1$ and $K_2$ define the total refractive power of the cornea in the first meridian and the second meridian respectively, $K_{a1}$ and $K_{a2}$ define the refractive power of the anterior cornea side in the first meridian and the second meridian respectively, $K_{p1}$ and $K_{p2}$ define the refractive power of the posterior cornea side in the first meridian and the second meridian respectively, $R_{a1}$ and $R_{a2}$ define the radius of the anterior cornea side in the first meridian and the second meridian respectively, $R_{p1}$ and $R_{p2}$ define the radius of the posterior cornea side in the first meridian and the second meridian respectively, $n_0$ defines an index of refraction of air, $n_1$ defines an index of refraction of the cornea, $n_2$ defines an index of refraction of aqueous fluid, and defines the central thickness of the cornea, wherein the radii $R_a$, $R_{p1}$ and $R_{p2}$ and the thickness d are indicated in meters, and the refractive powers $K_1$, $K_2$, $K_{a1}$, $K_{a2}$, $K_{p1}$ and $K_{p2}$ are indicated in diopters.

18. The method according to claim 17, wherein $R_{p1}$ and $R_{p2}$ are further determined by:

d) taking into consideration determined anterior/posterior ratios $c_1$ and $c_2$ as follows:

$$R_{p1} = c_1 * R_{a1} \quad (4)$$

$$R_{p2} = c_2 * R_{a2}$$

with $$c1 = \frac{R'p1}{R'a1}$$

$$c2 = \frac{R'p2}{R'a2}$$

wherein $R'_{a1}$ and $R'_{a2}$ are radii of the anterior corneal side determined from depth scans or sectional images in the first meridian and the second meridian and $R'_{p1}$ and $R'_{p2}$ are radii of the posterior corneal side on the first meridian and the second meridian determined from depth scans or sectional images, and $R_{p1}$ and $R_{p2}$ represent resulting values from the keratometric or topographical measurement and from a depth scan or sectional image determinations of $R'_{a1}$, $R'_{a2}$, $R'_{p1}$ and $R'_{p2}$.

19. The method according to claim 17, further comprising arithmetically averaging the measured values after prior removal of "outliers" and then including arithmetically averaged values in the calculation of the total refractive powers $K_1$ and $K_2$ according to method step c).

20. The method according to claim 17, wherein the depth scan measurement or sectional image measurement of the radii of the cornea takes place by image processing.

21. The method according to claim 20, further comprising fitting functions to the anterior and posterior side of the cornea.

22. The method according to claim 17, further comprising fitting a circle to the anterior and posterior side of the cornea.

23. The method according to claim 22, wherein the circle lies symmetrical to a vertex.

24. The method according to claim 17, further comprising fitting a sphere to the anterior and posterior side of the cornea, on depth scans or sectional images taken along multiple meridians.

25. The method according to claim 24, wherein the sphere lies symmetrical to a vertex.

26. The method according to claim 17, further comprising recording sectional image measurements using Scheimpflug cameras or slit lamps, wherein the sectional images are recorded along at least one meridian.

27. The method according to claim 26, wherein the sectional images are recorded along multiple meridians.

* * * * *

UNITED STATES PATENT AND TRADEMARK OFFICE
CERTIFICATE OF CORRECTION

PATENT NO. : 9,622,659 B2  
APPLICATION NO. : 14/440801  
DATED : April 18, 2017  
INVENTOR(S) : Bajramovic et al.

Page 1 of 1

It is certified that error appears in the above-identified patent and that said Letters Patent is hereby corrected as shown below:

In the Specification

Column 6, Line 17, delete "1,376" and insert --1.376--

Column 7, Line 45, delete "along" and insert --on--

Column 7, Line 45, delete ", which", insert --the--

Column 9, Line 25, delete "with"

Column 9, Line 32, delete "c1", insert --$c_1$--

Column 9, Line 33, delete "c2", insert --$c_2$--

Signed and Sealed this  
Fourteenth Day of November, 2017

Joseph Matal  
*Performing the Functions and Duties of the*  
*Under Secretary of Commerce for Intellectual Property and*  
*Director of the United States Patent and Trademark Office*